(12) United States Patent
Omote (10) Patent No.: US 8,085,900 B2
(45) Date of Patent: Dec. 27, 2011

(54) METHOD FOR X-RAY WAVELENGTH MEASUREMENT AND X-RAY WAVELENGTH MEASUREMENT APPARATUS

(75) Inventor: Kazuhiko Omote, Akishima (JP)

(73) Assignee: Rigaku Corporation, Tokyo (JP)

( * ) Notice: Subject to any disclaimer, the term of this patent is extended or adjusted under 35 U.S.C. 154(b) by 0 days.

(21) Appl. No.: 12/645,016

(22) Filed: Dec. 22, 2009

(65) Prior Publication Data
US 2010/0111254 A1    May 6, 2010

Related U.S. Application Data

(63) Continuation of application No. 11/819,710, filed on Jun. 28, 2007, now abandoned.

(30) Foreign Application Priority Data

Jun. 29, 2006   (JP) .................................. 2006-180189

(51) Int. Cl.
*G21K 1/06* (2006.01)
(52) U.S. Cl. .......................................... 378/84; 378/85
(58) Field of Classification Search .................... 378/84, 378/85
See application file for complete search history.

(56) References Cited

U.S. PATENT DOCUMENTS

| | | | |
|---|---|---|---|
| 3,160,749 A * | 12/1964 | Spielberg | 378/85 |
| 4,567,605 A | 1/1986 | Bartels et al. | |
| 5,199,058 A | 3/1993 | Tani et al. | |
| 5,509,043 A * | 4/1996 | Van Der Sluis | 378/85 |
| 2006/0043964 A1 | 3/2006 | Watanabe et al. | |

FOREIGN PATENT DOCUMENTS

| | | |
|---|---|---|
| JP | 9-049811 A | 2/1997 |
| JP | 2005/140719 A | 2/2005 |

\* cited by examiner

*Primary Examiner* — Hoon Song
*Assistant Examiner* — Mona M Sanei
(74) *Attorney, Agent, or Firm* — Birch, Stewart, Kolasch & Birch, LLP (57) ABSTRACT

A Method for X-ray wavelength measurement and an X-ray wavelength measurement apparatus capable of determining absolute wavelength easily and carrying out wavelength measurement having high precision with a simple structure are provided. The present invention is a Method for X-ray wavelength measurement carried out by using a channel-cut crystal for wavelength measurement (20) in which two opposing cut planes are formed and the lattice constant of which is known, and the method diffracts X-ray in respective arrangements (−, +) and (+, −) of the channel-cut crystal for wavelength measurement (20), to determine the absolute wavelength of the X-ray from the difference between crystal rotation angles in respective arrangements. This makes the alignment simpler, and, when only a channel-cut crystal suitable for measurement can be prepared, X-ray wavelength measurement can be carried out easily and with high precision.

16 Claims, 9 Drawing Sheets

| PEAK | ENERGY (eV) | FWHM (eV) | INTENSITY |
|---|---|---|---|
| P1 | 8047.8286 | 2.286 | $5.1810 \times 10^6$ |
| P2 | 8045.350 | 3.13 | $4.4485 \times 10^5$ |
| P3 | 8028.0711 | 2.622 | $1.5887 \times 10^6$ |
| P4 | 8026.773 | 3.61 | $7.1662 \times 10^5$ |

Fig. 9

METHOD FOR X-RAY WAVELENGTH MEASUREMENT AND X-RAY WAVELENGTH MEASUREMENT APPARATUS

BACKGROUND OF THE INVENTION

1. Field of the Invention

The present invention relates to a method for X-ray wavelength measurement and X-ray wavelength measurement apparatus for carrying out X-ray wavelength measurement with high precision.

2. Description of the Related Art

Such an X-ray wavelength measurement apparatus for carrying out X-ray wavelength measurement with high precision by using a slit to narrow down the incident direction of X-ray, or by arranging two analyzing crystals has been conventionally known. In addition, there is such an instrument as allowing four analyzing crystals to be interlocked with gears in order to obtain high resolution (for example, JP-A-2005-140719).

An X-ray wavelength measurement apparatus as disclosed in JP-A-2005-140719 irradiates radiation light as primary X-ray to a sample, and spectrally reflects fluorescent X-ray generated from the sample with four analyzing crystals in (+, −, −, +) arrangement to measure the intensity with a detector. Then, while changing the wavelength of the fluorescent X-ray spectrally reflected with the analyzing crystals by an interlocking means for interlocking the analyzing crystals and the detector, the apparatus guides the fluorescent X-ray into the detector. In this way, the resolution of the fluorescent X-ray spectrum is improved.

However, when such an X-ray wavelength measurement apparatus as described above is used, a slit is separately used to adjust strictly a diffraction angle θ for the purpose of determining absolute wavelength. Consequently, for the alignment to adjust a standard position, a special technique is required, and the measurement can not be carried out simply. Further, an X-ray wavelength measurement apparatus of two-crystal arrangement, which utilizes the arrangement of two planar analyzing crystals, needs an interlocking mechanism and results in a complex structure.

SUMMARY OF THE INVENTION

The present invention is achieved with the view of such circumstances, and aims to provide a method for X-ray wavelength measurement and an X-ray wavelength measurement apparatus for easily determining absolute wavelength and carrying out precise wavelength measurement with a simple structure. The present invention relates to an X-ray absolute angle spectroscopic instrument that uses the halved value of added measurement values of angles in plus and minus directions of two channel-cut crystals.

(1) In order to attain the above objects, the method for X-ray wavelength measurement according to the present invention is a method for X-ray wavelength measurement carried out by using a channel-cut crystal for wavelength measurement on which two opposing cut planes are formed and the lattice constant of which is known, and the method is characterized by comprising the steps of: diffracting X-ray in respective arrangements of (−, +) and (+, −) with the channel-cut crystal for wavelength measurement; and determining the absolute wavelength of X-ray from the difference between crystal rotation angles in the respective arrangements.

As described above, in the Method for X-ray wavelength measurement of the present invention, by diffracting and spectrally reflecting X-ray in respective arrangements (−, +) and (+, −) of the channel-cut crystal for wavelength measurement, it is possible to determine the zero point of the crystal rotation angle. Consequently, as compared with the conventional method which requires precise position adjustment by using a slit, the alignment becomes simpler. As the result, when only a channel-cut crystal suitable for measurement can be prepared, the measurement can be carried out easily with high precision.

(2) The Method for X-ray wavelength measurement according to the present invention is the Method for X-ray wavelength measurement, carried out by using a channel-cut crystal for collimator which is arranged on an X-ray incident side of the channel-cut crystal for wavelength measurement and in which two opposing cut planes are formed, and the method is further characterized by comprising the steps of: diffracting X-ray at a crystal plane having the same index as that of a crystal plane at which the channel-cut crystal for wavelength measurement diffracts X-ray at respective cut planes of the channel-cut crystal for collimator; and guiding the diffracted X-ray into the channel-cut crystal for wavelength measurement to carry out wavelength measurement.

Consequently, when X-ray to be spectrally reflected is divergent light, the X-ray is diffracted in different angles for respective wavelengths by the channel-cut crystal for collimator to enter a channel-cut crystal for wavelength measurement. As the result, it is possible to carry out X-ray wavelength measurement without interlocking the rotation of the channel-cut crystal for collimator with the channel-cut crystal for wavelength measurement.

(3) The X-ray wavelength measurement apparatus according to the present invention comprises: a channel-cut crystal for wavelength measurement in which two opposing cut planes are so formed that at least a part of mutual projections thereof overlap with the cut planes; and a detector for detecting the intensity of X-ray spectrally reflected by the channel-cut crystal for wavelength measurement, wherein a rotation center of the channel-cut crystal for wavelength measurement is set to be capable of diffracting X-ray in respective arrangements of (−, +) and (+, −).

As described above, in the X-ray wavelength measurement apparatus of the present invention, the channel-cut crystal for wavelength measurement has a rotation center so set that it can diffract X-ray in the arrangement of (−, +) and (+, −). Consequently, it is possible to carry out wavelength measurement in above two arrangements to determine precisely the diffraction angle from the difference of crystal rotation angles, and therefore the alignment becomes simpler as compared with the conventional method that requires precise position adjustment by using a slit. Further, since it is not necessary to interlock the channel-cut crystal upon carrying out X-ray wavelength measurement, the mechanism can be made simple. In addition, the X-ray wavelength measurement apparatus for wavelength measurement with setting two planer analyzing crystals in (+, +) arrangement have limitation on the diffraction angle of the analyzing crystal due to the interference of respective parts of the instrument, but in the X-ray wavelength measurement apparatus of the present invention, the position of the X-ray detector does not need to be largely moved, and, by preparing analyzing crystals suitable for respective diffraction angles, the diffraction angle is not limited.

(4) The X-ray wavelength measurement apparatus according to the present invention is characterized by further comprising a channel-cut crystal for collimator which is arranged on the incident side of the channel-cut crystal for wavelength measurement and in which two opposing cut planes are formed, wherein the channel-cut crystal for collimator diffracts X-ray at a crystal plane having the same index as that of a crystal plane at which the channel-cut crystal for wavelength measurement diffracts X-ray, to guide the diffracted X-ray into the channel-cut crystal for wavelength measurement.

Consequently, when X-ray to be spectrally reflected is divergent light, the X-ray is diffracted in different angles for respective wavelengths by the channel-cut crystal for collimator to enter the channel-cut crystal for wavelength measurement. As the result, it is possible to carry out X-ray wavelength measurement without interlocking the rotation of the channel-cut crystal for collimator with the channel-cut crystal for wavelength measurement, and to make the structure of the instrument simple.

(5) The X-ray wavelength measurement apparatus according to the present invention is characterized in that the channel-cut crystal for collimator is placed so that the rotation can be fixed for the incident X-ray upon carrying out wavelength measurement.

As described above, it is possible to carry out X-ray wavelength measurement, for a divergent light source, only by adjusting the rotation of the channel-cut crystal for wavelength measurement without interlocking the rotation of the channel-cut crystal for collimator with the channel-cut crystal for wavelength measurement. Consequently, the structure of the instrument can be made simple.

(6) The X-ray wavelength measurement apparatus according to the present invention is characterized in that the rotation center of the channel-cut crystal for wavelength measurement is set between two cut planes of the channel-cut crystal for wavelength measurement or between extended planes thereof; and a cut plane on which X-ray is incident when the channel-cut crystal for wavelength measurement diffracts the X-ray in the arrangement of (−, +) differs from that on which X-ray is incident when the channel-cut crystal for wavelength measurement diffracts the X-ray in the arrangement of (+, −).

As described above, in the X-ray wavelength measurement apparatus of the present invention, the rotation center of the channel-cut crystal for wavelength measurement is set between two cut planes of the channel-cut crystal for wavelength measurement or between extended planes thereof. Consequently, when X-ray is made diffracted in the arrangements (−, +) and (+, −) of the channel-cut crystal for wavelength measurement, it is possible to guide X-ray into different cut planes in the respective arrangements for wavelength measurement, and to measure absolute wavelength with high precision from the difference between respective crystal rotation angles even for a small diffraction angle.

(7) The X-ray wavelength measurement apparatus according to the present invention is characterized in that the rotation center of the channel-cut crystal for wavelength measurement is set in a position allowing X-ray to enter the identical cut plane when the channel-cut crystal for wavelength measurement diffracts the X-ray in either arrangement of (−, +) or (+, −).

As described above, in the X-ray wavelength measurement apparatus of the present invention, the rotation center of the channel-cut crystal for wavelength measurement is so set that X-ray can enter the identical cut plane when the crystal diffracts the X-ray in either arrangement (−, +) or (+, −), therefore, even for high diffraction angles, absolute wavelength can be measured with high precision from the difference between respective crystal rotation angles. In addition, for a high diffraction angle, $\delta\lambda/\lambda$ ($=\delta\theta/\tan\theta$) becomes small, therefore wavelength resolution can be improved.

(8) The X-ray wavelength measurement apparatus according to the present invention is characterized by further comprising a rotation control mechanism for controlling the rotation of the channel-cut crystal for wavelength measurement, wherein the rotation control mechanism includes an angle detector having self-calibration function for detecting the displacement of the scale position of the rotation angle.

As described above, since the X-ray wavelength measurement apparatus of the present invention is provided with an angle detector having self-calibration function, it can detect the displacement of the scale position of the rotation angle of the channel-cut crystal for wavelength measurement and calibrate absolute wavelength. Further, it can also evaluate how much degree of inaccuracy exists in the obtained absolute wavelength.

According to the Method for X-ray wavelength measurement of the present invention, since the zero point of the crystal rotation angle can be determined by rotating the channel-cut crystal for wavelength measurement to diffract and spectrally reflect X-ray in respective arrangements of (−, +) and (+, −), the alignment becomes simpler as compared with the conventional method which requires precise position adjustment by using a slit. As the result, when only a channel-cut crystal suitable for measurement is prepared, the measurement can be carried out easily with high precision.

According to the X-ray wavelength measurement apparatus of the present invention, since the zero point of the crystal rotation angle can be determined by diffracting and spectrally reflecting X-ray in the arrangements where the channel-cut crystal for wavelength measurement is set in (−, +) and (+, −) respectively, the alignment becomes simple. Further, there is no necessity to interlock the channel-cut crystal for collimator, thus making the mechanism simple. Furthermore, an X-ray wavelength measurement apparatus with two planer analyzing crystals that carries out wavelength measurement in an arrangement of (+, +) has limitation on the diffraction angle of the analyzing crystal due to the position of the X-ray detector, but the X-ray wavelength measurement apparatus of the invention does not need large movement of the position of the detector and is not limited by diffraction angles by preparing analyzing crystals suitable for respective diffraction angles.

DETAILED DESCRIPTION OF THE INVENTION

Best Modes for Carrying Out the Invention

Next, embodiments of the present invention will be described with reference to the drawings. To facilitate understanding of the description, the same reference numeral is given to the same constituent and overlapping description is omitted.

Embodiment 1

Figure 1:
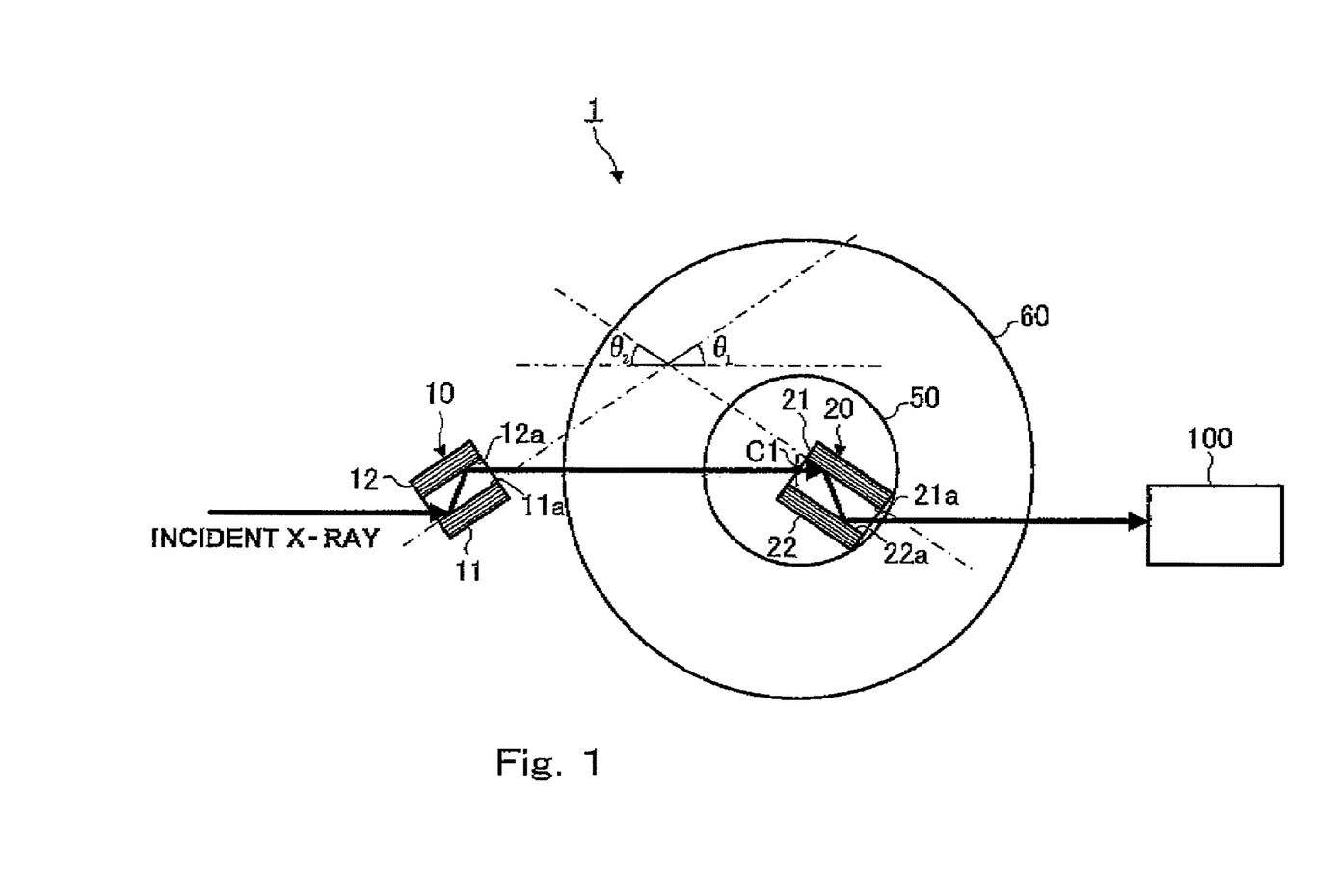
FIG. 1 is a plan view showing the outline of an X-ray wavelength measurement apparatus of an embodiment 1.

FIG. 1 is a plan view showing the outline of the configuration of an X-ray wavelength measurement apparatus 1 according to the present invention. As shown in FIG. 1, the X-ray wavelength measurement apparatus 1 includes a channel-cut crystal for collimator 10, a channel-cut crystal for wavelength measurement 20, a rotatable platform 50, an angle detector 60 and an X-ray detector 100. The channel-cut crystal is prepared by carving grooves to a unitary crystal block, and the parallel walls on both sides thereof are utilized for reflection, that is, diffraction. For the channel-cut crystal, the whole is composed of unitary crystal, and therefore all X-rays Bragg-reflected by one crystal wall cause Bragg reflection by the other crystal wall. The X-ray wavelength measurement apparatus 1 spectrally reflects X-ray having a specified wavelength out of incident X-ray having a continuous spectrum, and measures the intensity thereof with the X-ray detector 100. The X-ray wavelength measurement apparatus 1 can be applied to, for example, a state analysis instrument by spectroscopy and an X-ray wavelength precise measuring instrument.

The channel-cut crystal for collimator 10 is arranged on the X-ray incident side of the channel-cut crystal for wavelength measurement 20, and has a first crystal wall 11 and a second crystal wall 12. At respective crystal walls, a first cut plane 11a and a second cut plane 12a facing each other are formed. The channel-cut crystal for collimator 10 is fixed on a platform (not shown) at a position where X-ray being an object to be spectrally reflected enters to be diffracted. When X-ray to be spectrally reflected is divergent light, the X-ray is diffracted in different angles for respective wavelength by the fixed channel-cut crystal for collimator to enter the channel-cut crystal for wavelength measurement. Accordingly, in the X-ray wavelength measurement apparatus 1, it is possible to carry out X-ray wavelength measurement without interlocking the rotation of the channel-cut crystal for collimator 10 with the channel-cut crystal for wavelength measurement 20. Accordingly, the structure of the instrument can be made simple. Further, when X-ray to be spectrally reflected is parallel light such as radiation from synchrotron source, the channel-cut crystal for collimator may be omitted to make the configuration simpler.

The Bragg angle of the channel-cut crystal for collimator 10 is represented as $\theta_1$ in FIG. 1. The channel-cut crystal for collimator is so arranged that X-ray having been diffracted by the channel-cut crystal for collimator 10 enters the channel-cut crystal for wavelength measurement 20. The channel-cut crystal for collimator 10 may have such figure and arrangement that allow X-ray to be diffracted at a crystal plane having the same index as that of a crystal plane at which the channel-cut crystal for wavelength measurement 20 allows X-ray to be diffracted, so that the X-ray may enter the channel-cut crystal for wavelength measurement 20. The number of diffraction at the channel-cut crystal is at least two, may be four or six, and there is no particular limitation on it. By increasing the number of the diffraction, a sharp peak having a cut tail can be detected. On the other hand, when emphasizing the assurance of intensity, the number of the diffraction may be decreased.

Incidentally, although the channel-cut crystal for collimator 10 is fixed on the platform during the spectrum measurement, it is so designed that the adjustment of the angle prior to the measurement is possible. The adjustment may be practiced either manually or automatically. In any event, the channel-cut crystal for collimator 10 is independent of the rotation control of the channel-cut crystal for wavelength measurement 20 to be described.

The channel-cut crystal for wavelength measurement 20 has a third crystal wall 21 and a fourth crystal wall 22. At respective crystal walls, a third cut plane 21a and a fourth cut plane 22a facing each other are formed. In addition, the projection of the cut plane 21a to the cut plane 22a and the cut plane 22a are so formed that at least a part of these overlap with each other. That is, when the channel-cut crystal for wavelength measurement is viewed from the side, the crystal walls 21 and 22 overlap with no interspace. This makes it possible to rotate the channel-cut crystal for wavelength measurement 20 to diffract X-ray in respective arrangements of (−, +) and (+, −).

The arrangement of (+) or (−) indicates an arrangement of a crystal that diffracts X-ray in the bending direction determined by regarding the bending direction of the first diffraction as (+). Accordingly, an arrangement of a crystal that diffracts X-ray in the same bending direction as that in the first diffraction is (+), and an arrangement of a crystal that diffracts X-ray in the bending direction reverse to that of the first diffraction is (−).

The channel-cut crystal for spectroscopy 20 is provided at a position where X-ray having been diffracted by the channel-cut crystal for collimator 10 on the turn table 50 can enter. The channel-cut crystal for spectroscopy 20 has the rotation center C1 that is set so as to be capable of diffracting X-rays in an arrangement of (−, +) and (+, −) relative to the incident X-ray. That is, the rotation center C1 is set at a position where X-rays are not intercepted by the crystal wall 21 or 22 when either one of the above arrangements is taken, and X-rays are not prevented from reaching the cut plane in either one of the arrangements.

As described above, the rotation center C1 thereof is set in the channel-cut crystal for wavelength measurement 20 so as to make it possible to diffract X-ray in arrangements of (−, +) and (+, −). As described above, since it is possible to carryout the spectral reflection in the arrangement to determine the zero point of the crystal rotation angle, the alignment becomes simpler as compared with the conventional method that requires precise position adjustment by using a slit.

In an example in FIG. 1, the rotation center C1 is set between the cut planes 21a and 22a. The cut plane 21a on which X-ray is incident when the channel-cut crystal for wavelength measurement 20 takes the (−, +) arrangement, and the cut plane 22a on which X-ray is incident when the channel-cut crystal for wavelength measurement 20 takes the (+, −) arrangement are different from each other. In other words, for the cut plane 21a, (−) diffraction occurs in either arrangement, and for the cut plane 22a, (+) diffraction occurs in either arrangement. Here, the rotation center C1 may be set between the extended planes of respective cut planes. The Bragg angle of the channel-cut crystal for wavelength measurement 20 is represented by $\theta_2$ in FIG. 1.

Analyzing crystals that can be used for the channel-cut crystal for collimator 10 or the channel-cut crystal for wavelength measurement 20 include Si and Ge, but are not limited to these. As to crystal planes for use in spectral reflection, for example, Si (400), Si (220), Si (440), Si (111), Si (333) and Si (444) can be mentioned. The rotatable platform 50 is connected to a rotary driving instrument (not shown) capable of rotating at intervals of a minute angle. The rotary driving instrument uses a servo motor, a stepping motor or the like.

The angle detector 60 is a detector for measuring the rotation angle of the channel-cut crystal for wavelength measurement 20 by counting the scale carved to a circular disc with a reading head. The angle detector 60 uses, for example, a common rotary encoder. The rotatable platform 50, the angle detector 60 and the X-ray detector 100 are controlled by a controlling section (not shown).

The X-ray detector 100 is arranged at a position on which the X-ray diffracted by the channel-cut crystal for wavelength measurement 20 is incident. In the present invention, there is no need to move largely the position of the X-ray detector to eliminate the limitation on the angle caused by the interference of respective sections. The X-ray detector 100 detects the intensity of the X-ray spectrally reflected by the channel-cut crystal. The position of the X-ray detector 100 can be moved corresponding to the incident position of the X-ray. Incidentally, the X-ray detector 100 may use the one having a large detection range, being fixed and used at a predetermined position.

Figure 2A:
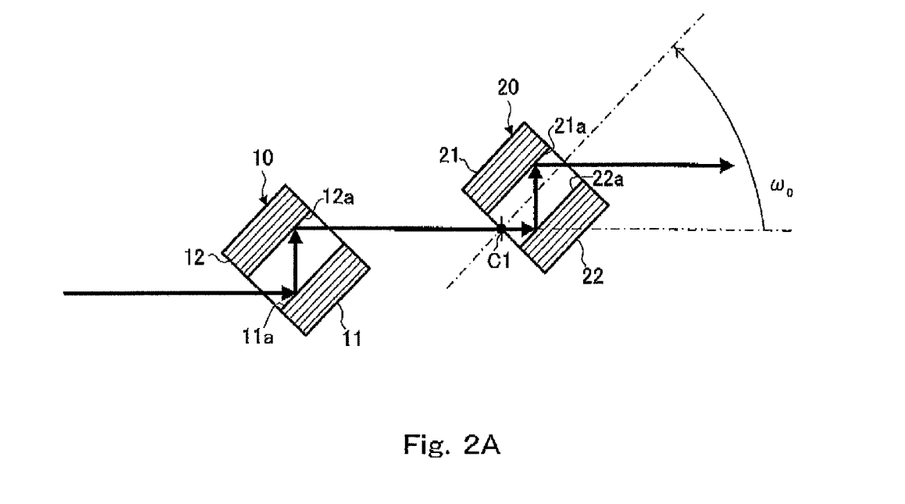
FIG. 2A is a plan view showing a channel-cut crystal for wavelength measurement in an arrangement of (+, −).

Next, a method for X-ray wavelength measurement by using the aforementioned X-ray wavelength measurement apparatus 1 will be described. Firstly, from a crystal having a known lattice constant, two channel-cut crystals are prepared in which a cut plane is formed so as to diffract X-ray at the identical crystal plane. One of these is set on a platform as the channel-cut crystal for collimator 10, and the other is set on the rotatable platform 50 as the channel-cut crystal for wavelength measurement 20. Then, the channel-cut crystal for collimator 10 is adjusted and fixed so as to diffract X-ray having required range of wavelength in the direction of channel-cut crystal for wavelength measurement 20. On the other hand, the channel-cut crystal for wavelength measurement 20 is fixed on the rotatable platform 50 so that the rotation center C1 lies between the cut planes 21a and 22a. Then, the rotatable platform 50 is rotated to set the channel-cut crystal for wavelength measurement 20 in such arrangement that causes (+, −) diffraction as shown in FIG. 2A.

Subsequently, by guiding X-ray for spectral reflection, firstly, wavelength measurement is carried out in such setting that the channel-cut crystal for wavelength measurement 20 has an arrangement of (+, −) to diffract X-ray. That is, the arrangement is set so that the diffraction by respective channel-cut crystals is (+, −, +, −), and the X-ray is diffracted in the order of cut planes 11a, 12a, 22a and 21a. On this occasion, in case where diffraction is carried out by using the identical crystal plane for the channel-cut crystal for collimator and for the channel-cut crystal for wavelength measurement, a sharp peak can be obtained when two crystal planes become strictly parallel to each other. As described above, the peak angle position $\omega_0$ of the X-ray intensity having been detected with the X-ray detector 100 is detected with the angle detector 60. The peak angle position $\omega_0$ is the origin position of the channel-cut crystal for wavelength measurement.

Figure 2B:
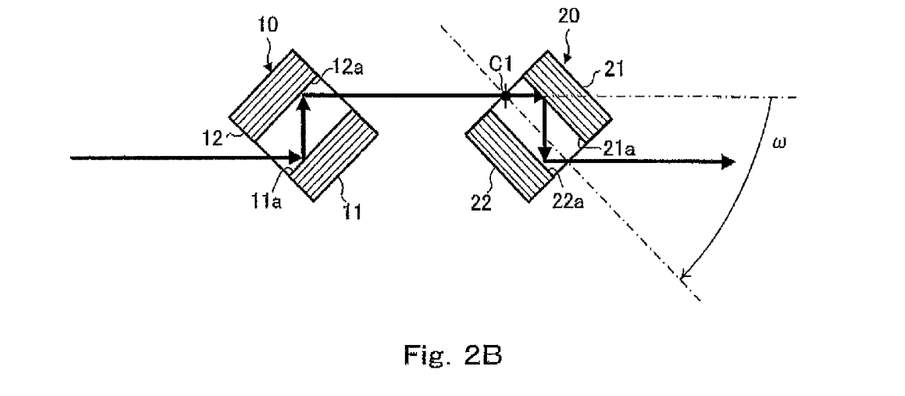
FIG. 2B is a plan view showing the channel-cut crystal for wavelength measurement in an arrangement of (−, +).

Next, the channel-cut crystal for wavelength measurement 20 is set to an arrangement that diffracts X-ray in (−, +) as shown in FIG. 2B. That is, respective channel-cut crystals are arranged so as to give (+, −, −, +) diffractions, respectively, and the X-ray is diffracted in the order of cut planes 11a, 12a, 21a and 22a. Then, from the X-ray intensity detected by the X-ray detector 100 and the angle $\omega$ detected by the angle detector 60, an X-ray spectrum with high resolution is obtained. Incidentally, the angle detected by the angle detector 60 can be obtained by measuring the rotation amount of the rotation platform or the rotation axis (shaft) from the reference rotation position with the angle detector 60, which corresponds to the crystal rotation angle. The method for determining angles $\omega$ and $\omega_0$ as shown in the drawing is an example, and there is no particular limitation on the method for determining the angle when the angle represents the rotation angle of the crystal.

The origin of the angle $\omega$ detected by the angle detector 60 in the measured spectrum is the above-described $\omega_0$. Accordingly, the difference between both angles $\omega - \omega_0$ is the rotation angle of the channel-cut crystal for wavelength measurement, and Bragg angle $\theta$ of the channel-cut crystal for wavelength measurement on this occasion is represented by $\theta = (\omega - \omega_0)/2$. When representing the lattice spacing of the channel-cut crystal for wavelength measurement by d, the angle $\theta$ on the horizontal axis of a measured spectrum can be converted to the wavelength $\lambda$ of X-ray according to the formula of $\lambda = 2d \cdot \sin \theta$. Further, the wavelength $\lambda$ (Å) of X-ray is converted to energy E (eV) according to the formula of $E = 12398.419/\lambda$.

In this way, the absolute wavelength of spectrally reflected X-ray can be detected. As described above, X-ray is diffracted in respective arrangements in which two channel-cut crystals are set to (+, −, −, +) and (+, −, +, −) by rotating the channel-cut crystal for wavelength measurement 20 to carry out spectral reflection and determine the origin of the crystal rotation angle, therefore the alignment becomes simpler as compared with conventional method that requires precise position adjustment by using a slit. As the result, when only suitable channel-cut crystals are prepared, X-ray wavelength measurement can be carried out easily with high precision.

Embodiment 2

Figure 3:
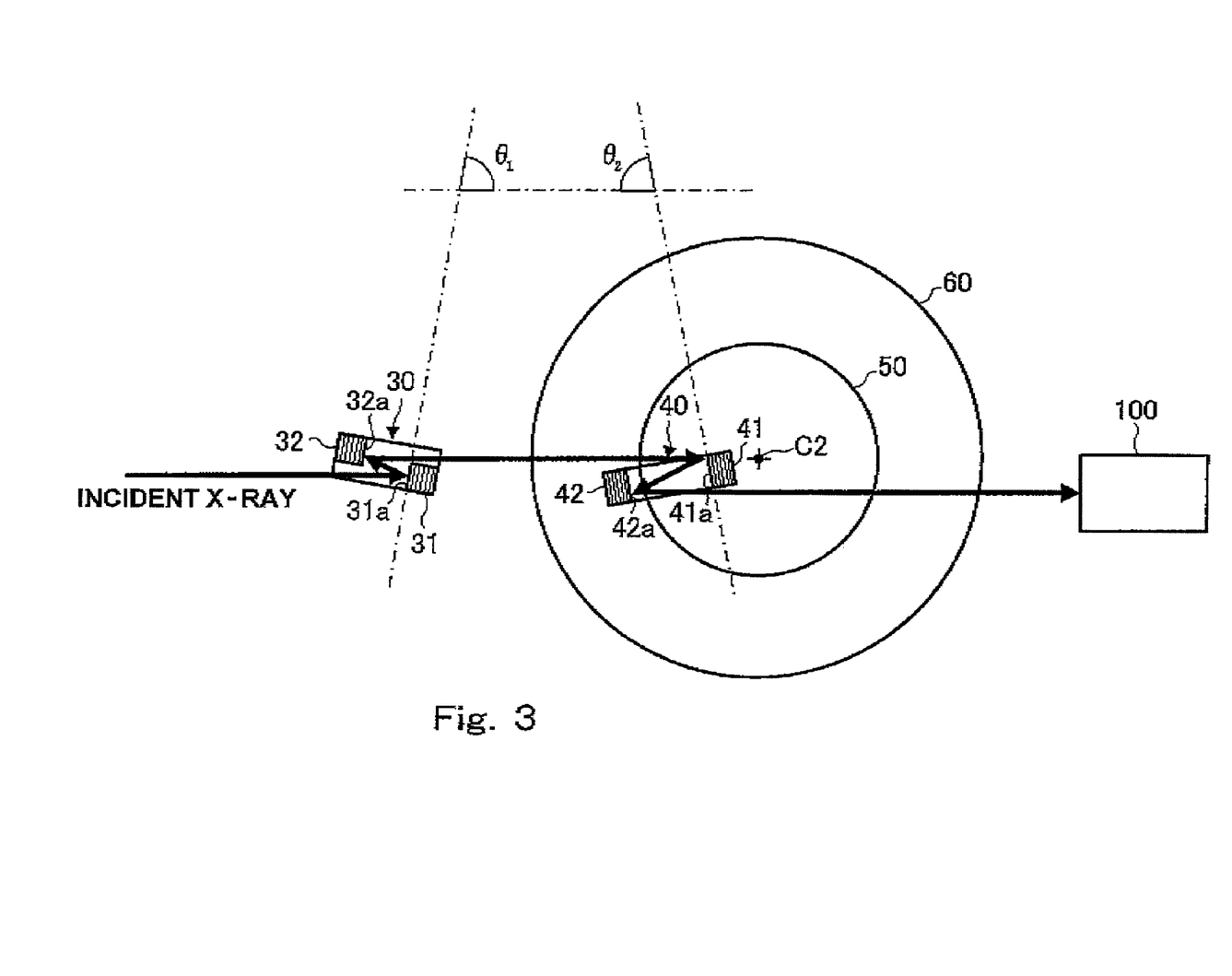
FIG. 3 is a plan view showing the outline of an X-ray wavelength measurement apparatus of an Embodiment 2.
Figure 4:
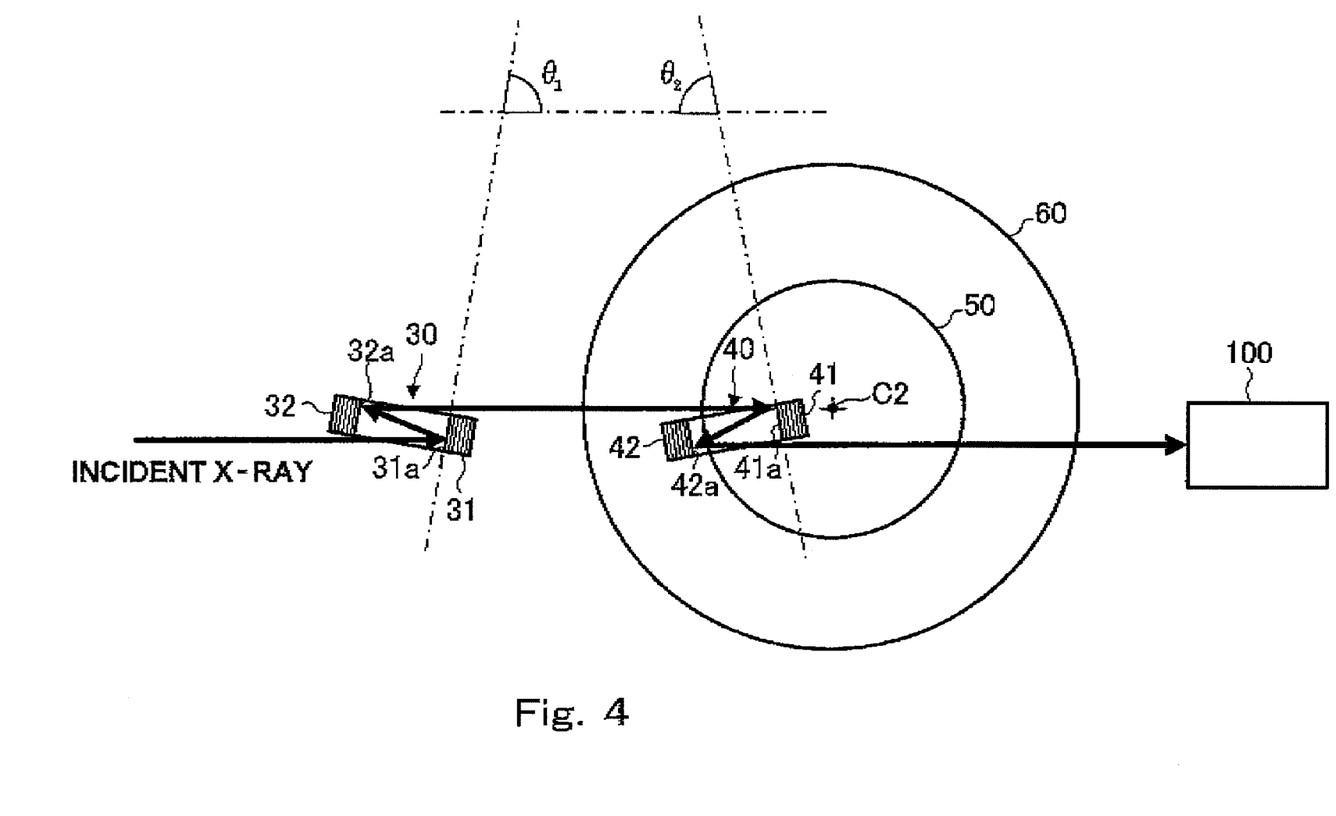
FIG. 4 is a plan view showing the outline of the X-ray wavelength measurement apparatus of the Embodiment 2.

In the above-described Embodiment 1, the rotation center C1 is so provided that X-ray enters different cut planes when the channel-cut crystal for wavelength measurement 20 is set to respective arrangements of (+, −) and (−, +), but the rotation center may be provided so that X-ray may enter the identical cut plane. FIG. 3 is a schematic drawing showing the X-ray wavelength measurement apparatus 1 in which the channel-cut crystal for wavelength measurement is so arranged that X-ray enters the identical cut plane. A channel-cut crystal for collimator 30 has a first crystal wall 31 and a second crystal wall 32, and, at respective crystal walls, a first cut plane 31a and a second cut plane 32a facing each other are formed. The lengths of respective crystal walls are shortened in different directions in accordance with the passing channels of X-ray beams so that a large diffraction angle can be obtained. For a scheme to obtain a large diffraction angle, as shown in FIG. 4, crystals, in which mutual distance is enlarged relative to the length thereof without shortening the lengths of the crystal wall 31 and the crystal wall 32, may be employed.

A channel-cut crystal for wavelength measurement 40 has a third crystal wall 41 and a fourth crystal wall 42, and, at respective crystal walls, a third cut plane 41a and a fourth cut plane 42a facing each other are formed. In the channel-cut crystal for wavelength measurement 40, a crystal, in which the mutual distances of respective crystal walls 31 and 32 are enlarged relative to the lengths of these, is employed so as to obtain a large diffraction angle. These two opposing cut planes 41a and 42a are so formed that at least a part of respective projections overlap with the cut planes. This makes it possible to rotate the channel-cut crystal for wavelength measurement 40 to diffract X-ray in respective arrangements of (−, +) and (+, −).

In the example in FIG. 3, a rotation center C2 of the channel-cut crystal for wavelength measurement is set outside the cut plane 41a. Then, the rotation center C2 is set at a position where X-ray is not shielded by the crystal wall 42 when either of the above arrangements occurs and X-ray reaches the cut plane 41a in either arrangement. The cut plane 41a on which X-ray enters when the channel-cut crystal for wavelength measurement 40 diffracts the X-ray in an arrangement of (−, +), and the cut plane 41a on which X-ray enters when the channel-cut crystal for wavelength measurement 40 diffracts the X-ray in an arrangement of (+, −) are identical. As described above, the rotation center of the channel-cut crystal for wavelength measurement 40 is set at a position that allows X-ray to enter the identical cut plane 41a in both cases where X-ray is diffracted in either arrangement of (−, +) or (+, −), therefore absolute wavelength can be measured for high diffraction angles with high precision. For high diffraction angles, $\delta\lambda/\lambda$ becomes small, therefore high wavelength resolution can be obtained. On this occasion, the cut plane 41a leads to carry out the diffraction in (−) direction in one arrangement, and the diffraction in (+) direction in the other arrangement.

Figure 5A:
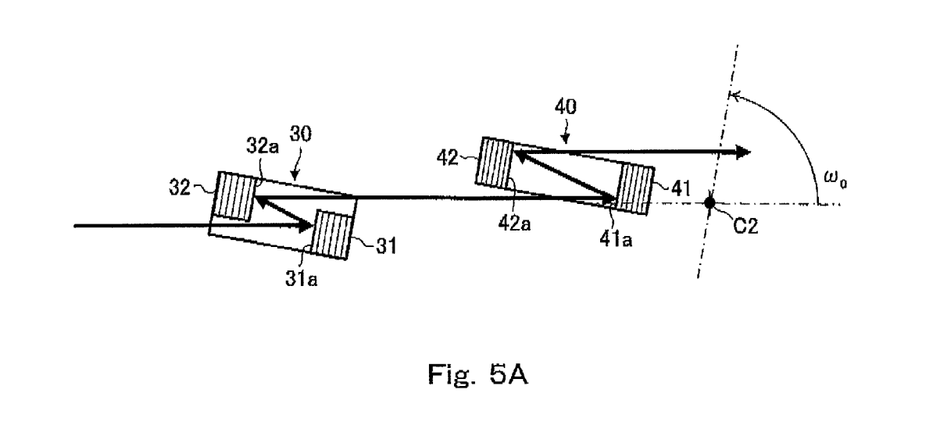
FIG. 5A is a plan view showing the channel-cut crystal for wavelength measurement in an arrangement of (+, −).

Next, a method for carrying out X-ray wavelength measurement in the above-described crystal arrangement will be described. Firstly, two channel-cut crystals, in which a cut plane has been formed so as to be capable of diffracting X-ray at the identical crystal plane, are prepared from a crystal having a known lattice constant, and these are set on a platform and on the rotatable platform 50 as a channel-cut crystal for collimator and a channel-cut crystal for wavelength measurement, respectively. The channel-cut crystal for wavelength measurement 40 is so fixed on the rotatable platform 50 that the rotation center C2 lies near the crystal wall 41. Firstly, the channel-cut crystal for wavelength measurement 40 is set to an arrangement for causing (+, −) diffraction, as shown in FIG. 5A.

Then, by guiding X-ray for spectral reflection, firstly, the channel-cut crystal for wavelength measurement 40 diffracts the X-ray in the arrangement of (+, −) to carry out wavelength measurement. That is, respective channel-cut crystals are arranged so as to be (+, −, +, −) to allow X-ray to be diffracted in the order of cut planes 31a, 32a, 41a and 42a. On this occasion, in case where the diffraction is carried out by using the identical crystal plane for the channel-cut crystal for collimator and for the channel-cut crystal for wavelength measurement, a sharp peak is obtained when two crystal planes become strictly parallel to each other. As described above, the peak angle position $\omega_0$ of X-ray intensity detected by the X-ray detector 100 is detected with the angle detector 60. The angle position $\omega_0$ is the origin point of the channel-cut crystal for wavelength measurement.

Figure 5B:
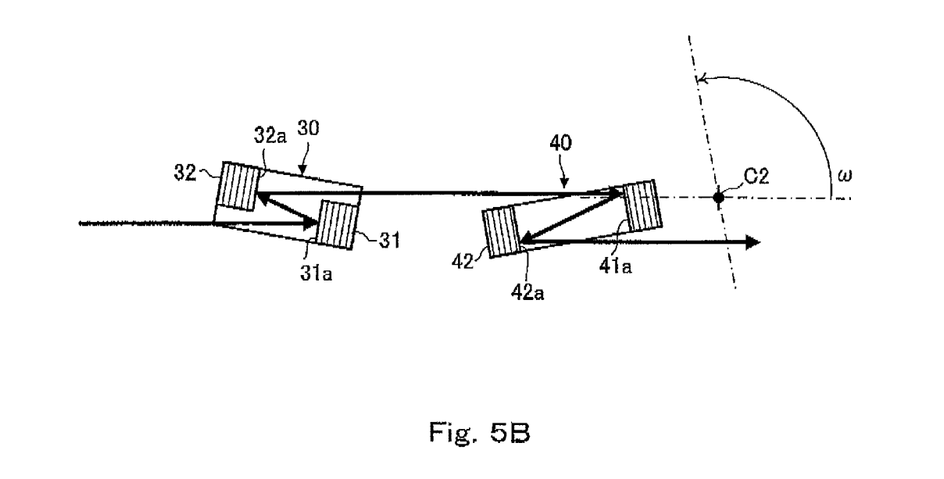
FIG. 5B is a plan view showing the channel-cut crystal for wavelength measurement in an arrangement of (−, +).

Next, the channel-cut crystal for wavelength measurement 40 is so arranged as to cause (−, +) diffraction as shown in FIG. 5B. That is, respective channel-cut crystals are so arranged as to cause (+, −, −, +) diffraction, and allow X-ray to be diffracted in the order of cut planes 31a, 32a, 41a and 42a. Then, from the X-ray intensity detected by the X-ray detector 100 and the angle $\omega$ detected by the angle detector 60, an X-ray spectrum with high resolution is obtained.

The origin of the angle $\omega$ detected by the angle detector 60 in the measured spectrum is above-described $\omega_0$. Accordingly, the difference in respective angles $\omega - \omega_0$ is the rotation angle of the channel-cut crystal for wavelength measurement, and Bragg angle $\theta$ of the channel-cut crystal for wavelength measurement on this occasion is represented by $\theta = \pi/2 - (\omega - \omega_0)/2$. When representing the lattice spacing of the channel-cut crystal for wavelength measurement by d, the angle $\theta$ on the horizontal axis of a spectrum can be converted to the wavelength $\lambda$ of X-ray according to the formula of $\lambda = 2d \cdot \sin\theta$. Further, the wavelength $\lambda$ (Å) of X-ray is converted to energy E (eV) according to the formula of $E = 12398.419/\lambda$.

The above is described for the case where X-ray to be spectrally reflected is divergent light, but in case where a spectrum of X-ray having been spectrally reflected to some extent or of such parallel light as synchrotron radiation source is measured, the channel-cut crystal for collimator may be omitted. On this occasion also, by measuring $\omega_0$ while arranging the channel-cut crystal for wavelength measurement in (−, +) followed by measuring $\omega$ while arranging it in (+, −), as is the case for the above, Bragg angle $\theta$ can be calculated correctly.

Embodiment 3

The above-described X-ray wavelength measurement apparatus 1 of the Embodiment 1 can measure absolute wavelength with high precision, but it is also possible to carry out precise calibration by giving additional self-calibration function to the angle detector.

Figure 6:
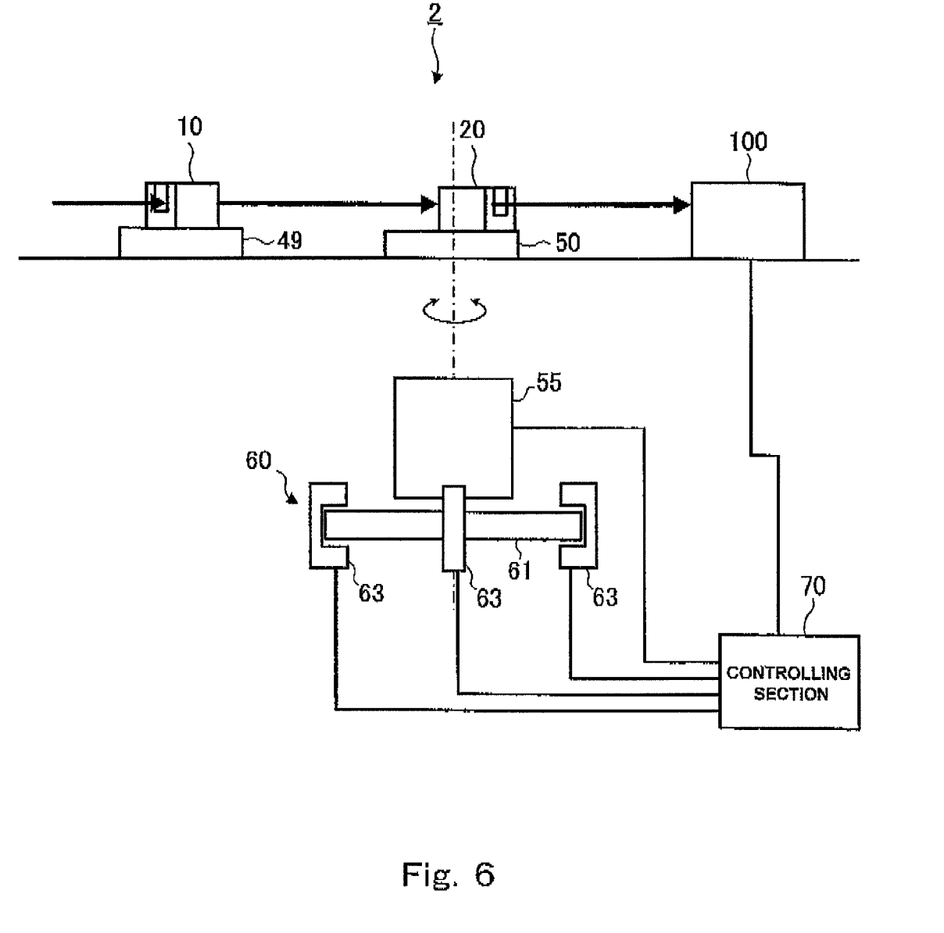
FIG. 6 is a side view showing the outline of an X-ray wavelength measurement apparatus of an Embodiment 3.

FIG. 6 is a side view showing an X-ray wavelength measurement apparatus 2 provided with an angle detector having self-calibration function. As shown in FIG. 6, the X-ray wavelength measurement apparatus 2 includes a channel-cut crystal for collimator 10, a channel-cut crystal for wavelength measurement 20, a fixed platform 49, a rotatable platform 50, a rotary driving instrument 55, an angle detector 60, a controlling section 70 and a detector 100. The rotary driving instrument 55, the angle detector 60 and the controlling section 70 constitute a rotation control mechanism.

The rotatable platform 50 is connected to the rotary driving instrument 55 capable of rotation at intervals of a minute angle. The rotary driving instrument 55 uses a servo motor, a stepping motor or the like.

The angle detector 60 is a detector for measuring a rotation angle by counting scales carved to a circular disc 61 with a reading head 63. The angle detector 60 uses a rotary encoder or the like.

Figure 7:
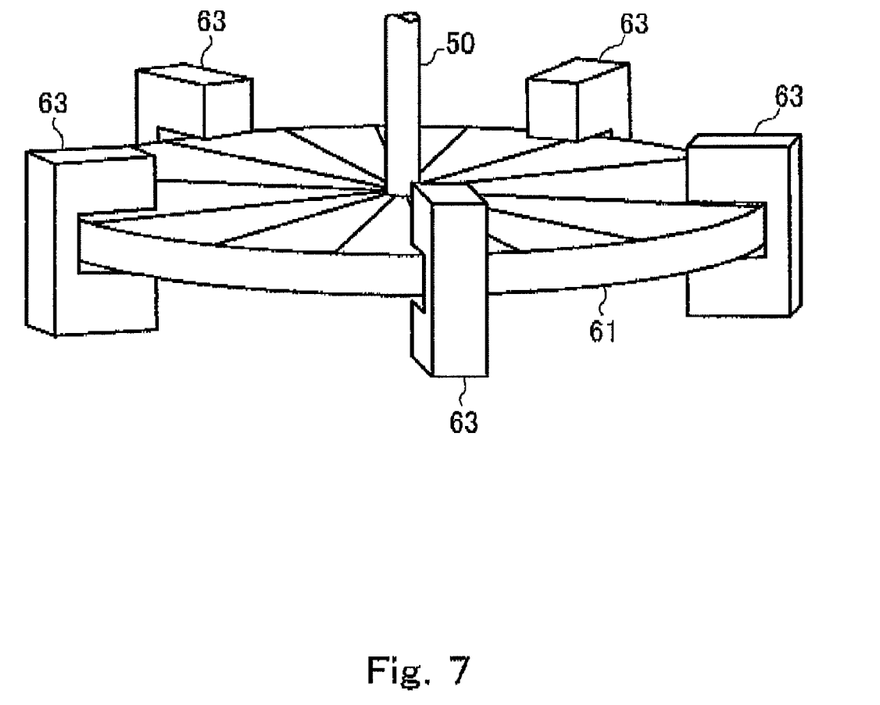
FIG. 7 is a perspective view of an angle detector used for the X-ray wavelength measurement apparatus of the Embodiment 3.

FIG. 7 is a perspective view of the angle detector 60 in the present invention. As shown in FIG. 7, the angle detector 60 includes a circular disc 61 to which scales are carved, a shaft 62 to which the circular disc 61 is fixed, and a reading head 63 set around the disc at even intervals. The reading head 63 is arranged around the circular disc 61 at even intervals.

The rotatable platform 50, the angle detector 60 and the X-ray detector 100 are controlled by the controlling section 70. The controlling section 70 is constituted of CPU and main memory, and, mainly, carries out the control of instruments and the calculation of numerical values.

Hereinafter, a method for obtaining the displacement of the scale position is described. The displacement of the angle signal of the scale i to be detected by the reading head 63 can be represented as $b_i$. Further, the displacement of the angle signal of the scale $i + j \cdot N/n$ at jth reading head 63 can be represented as $b_{i+j \cdot N/n}$. On this occasion, it is intended to indicate the number of reading heads arranged at even intervals by n, and the number of scales of the encoder by N.

When determining the 0th reading head 63 as the reference head, difference $\delta_{i,j}$ between the angle signal $b_{i+j\cdot N/n}$ of the jth head and the angle signal $b_i$ of the reference head, and the average value $\mu_{i,n}$ of these can be represented as follows.

$$\delta_{i,j} = b_{i+j\cdot N/n} - b_i \quad \text{(formula I)}$$

$$\mu_{i,n} = \frac{1}{n}\sum_{j=0}^{n-1}\delta_{i,j} = \frac{1}{n}\sum_{j=0}^{n-1}b_{i+j\cdot N/n} - b_i \quad \text{(formula II)}$$

The amount resulted from eliminating Fourier components of multiple number of n from $b_i$ can be obtained as follows.

$$\tilde{b}_{i,j} = b_i - \frac{1}{n}\sum_{j=0}^{n-1}b_{i+j\cdot N/n} = -\mu_{i,n} \quad \text{(formula III)}$$

The above-described $-\mu_{i,n}$ is the displacement of the scale position of the scale i. In this way, by seeking the measurement difference between the reference reading head 63 and respective reading heads and by obtaining the average value thereof, it is possible to calculate the displacement of the scale position and to carry out self-calibration. As described above, it is possible to calibrate the error of such angle information as the decentering of an attaching axis under use environments and the secular change of the angle detector. In addition, it is also possible to evaluate how much uncertainness is there in obtained absolute wavelength.

Experimental Example

An experiment of wavelength measurement was practiced by using the X-ray wavelength measurement apparatus of the Embodiment 1. The experimental method and the experimental results are described below as Experimental Example.

As an X-ray source, CuKα line was used, and as a channel-cut crystal, a Si analyzing crystal was used and Si (400) was used as the crystal plane.

Firstly, since the Bragg angle θ is approximately 34.5°, two channel-cut crystals having a suitable size and figure for the angle were prepared. One of these was fixed on a platform as the channel-cut crystal for collimator so that diffracted X-ray became approximately parallel to the incident X-ray, and the other was set on a rotatable platform as the channel-cut crystal for wavelength measurement. The rotation center of the channel-cut crystal for wavelength measurement was set so as to lie between two cut planes.

Then, by setting the channel-cut crystal for wavelength measurement to an arrangement of (+, −) and diffracting X-ray as shown in FIG. 2A, the profile of the CuKα peak of the X-ray was detected. When an identical crystal plane is used for the channel-cut crystal for collimator and for the channel-cut crystal for wavelength measurement to carry out the diffraction, a sharp peak is obtained when respective crystal planes become strictly parallel to each other. The peak angle poison of the channel-cut crystal for wavelength measurement on this occasion is indicated by $\omega_0$.

Next, by setting the channel-cut crystal for wavelength measurement to an arrangement of (−, +) and diffracting X-ray as shown in FIG. 2B, X-ray wavelength measurement profile with a high resolution was measured. On this occasion, the channel-cut was set to an arrangement of (+, −, −, +) to cause the diffraction.

The origin of the angle ω detected by the angle detector 60 in the measured spectrum is the above-described $\omega_0$. Therefore, the difference between both angles $\omega-\omega_0$ was calculated to obtain the rotation angle of the channel-cut crystal for wavelength measurement. Bragg angle θ of the channel-cut crystal for wavelength measurement on this occasion is $\theta=(\omega-\omega_0)/2$. When representing the lattice spacing of the channel-cut crystal for wavelength measurement by d, the angle θ on the horizontal axis of a spectrum is represented by a formula of $\lambda=2d\cdot\sin\theta$. According to the formula, the angle θ was converted to the wavelength λ of the X-ray. Further, the wavelength λ (Å) of X-ray was converted to energy E (eV) according to the formula of $E=12398.419/\lambda$.

Figure 8:
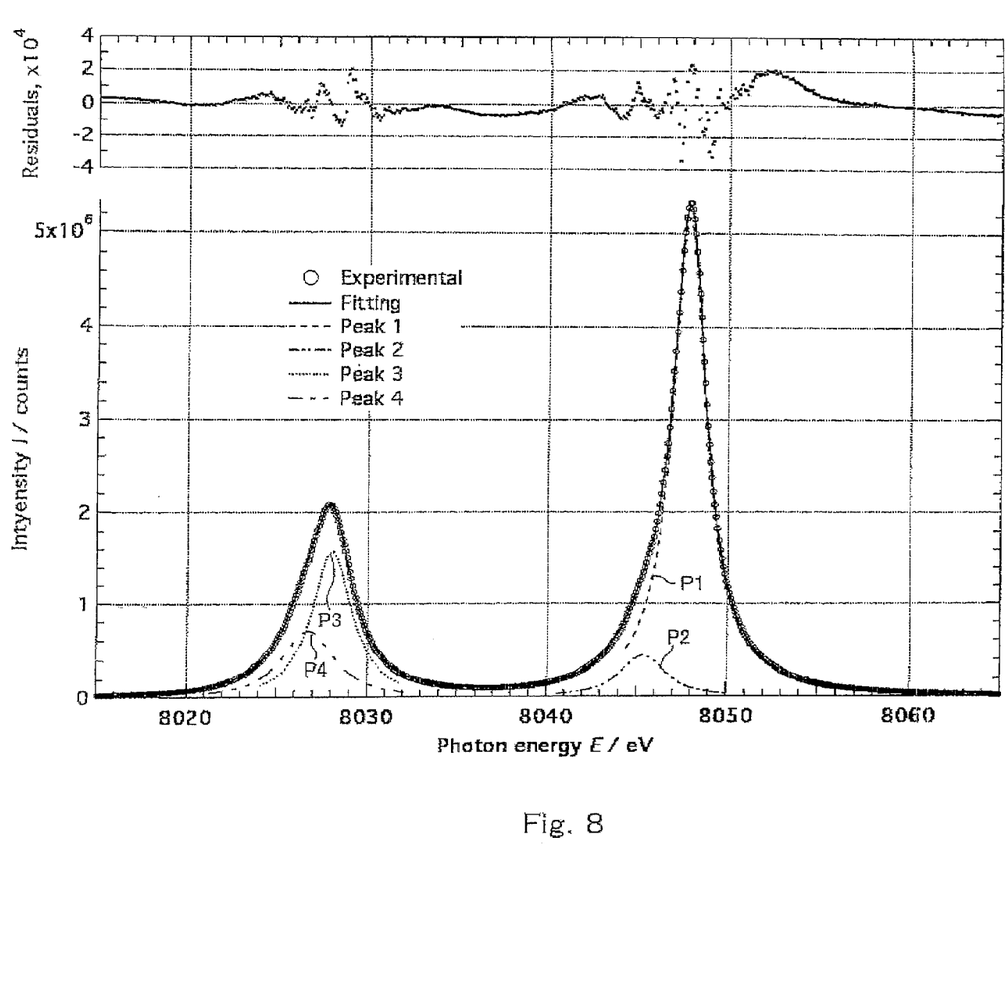
FIG. 8 is a profile showing the result of practicing a Method for X-ray wavelength measurement according to the present invention.

FIG. 8 is a profile showing the result of the above-described X-ray wavelength measurement. In the graph, a shows the X-ray intensity obtained by the experiment. Each of peaks P1 to P4 shows curve of Lorenz function representing peaks of CuKα1 and CuKα2 obtained by calculation, respectively. When subjecting these curves of Lorenz functions to fitting treatment, they coincided with the profile obtained by the experiment.

Figure 9:
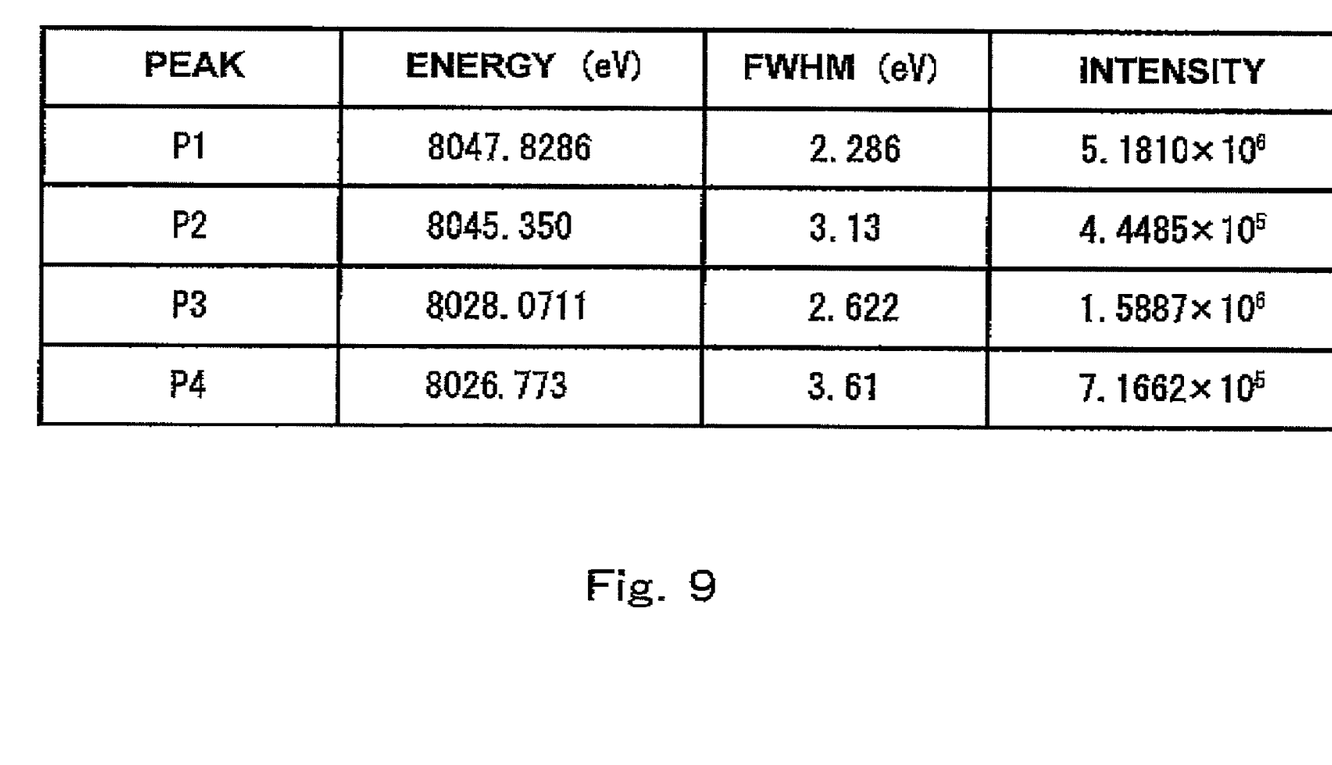
FIG. 9 is a drawing showing parameters of respective Lorenz functions.

Parameters of respective Lorenz functions thus obtained are shown in FIG. 9. The full width of Half Maximum 2.286 eV at the peak P1 is the highest resolution among those historically obtained. On this occasion, δE is considered to be 0.2 eV or less. Further, precise absolute wavelength of X-ray could be measured.

What is claimed is:

1. A method for X-ray wavelength measurement carried out by using a first channel-cut crystal for wavelength measurement in which two opposing cut planes are formed and the lattice constant of which is known, said method comprising the steps of:
   rotating, by utilizing a turntable, said first channel-cut crystal with respect to an incident X-ray beam direction in respective arrangements of (−, +) and (+, −) with said first channel-cut crystal, wherein (+) or (−) is defined as a crystal arrangement which causes a same or opposite X-ray bending direction to a first X-ray bending direction of diffraction; and
   determining an absolute wavelength of X-ray from a difference between crystal rotation angles in said respective arrangements.

2. The method for X-ray wavelength measurement according to claim 1, further comprising the steps of: collimating X-rays to be parallel light by a collimator arranged on an X-ray incident side of said first channel-cut crystal and then guiding the parallel light into said first channel-cut crystal to carry out wavelength measurement.

3. The method for X-ray wavelength measurement according to claim 1, wherein a second channel-cut crystal is placed for collimator which is arranged on an X-ray incident side of said first channel-cut crystal and in which two opposing cut planes are formed, said method further comprising the steps of:
   diffracting X-ray at a crystal plane having the same index as that of a crystal plane at which said first channel-cut crystal diffracts X-ray at respective cut planes of said second channel-cut crystal; and
   guiding the diffracted X-ray into said first channel-cut crystal to carry out wavelength measurement.

4. An X-ray wavelength measurement apparatus, comprising:
   a first channel-cut crystal for wavelength measurement in which two opposing cut planes are so formed that at least a part of mutual projections thereof overlap with the cut planes; a detector for detecting the intensity of X-ray spectrally reflected by said first channel-cut crystal; and turntable for rotating said first channel-cut crystal with respect to an incident X-ray beam direction such that a rotation center of said first channel-cut crystal is set to be capable of diffracting X-ray in respective arrangements of (−, +) and (+, −), wherein (+) or (−) is defined as a crystal arrangement which causes a same or opposite X-ray bending direction to a first X-ray bending direction of diffraction.

5. The X-ray wavelength measurement apparatus according to claim 4, further comprising a collimator arranged on an X-ray incident side of said first channel-cut crystal, wherein X-rays are collimated to be parallel light by said collimator and then guided into said first channel-cut crystal carry out wavelength measurement.

6. The X-ray wavelength measurement apparatus according to claim 4 wherein:
the rotation center of said first channel-cut crystal is set between said two opposing cut planes of said first channel-cut crystal or between extended planes of said two opposing cut planes; and
a cut plane on which X-ray is incident when said first channel-cut crystal diffracts the X-ray in the arrangement of (−, +) differs from that on which X-ray is incident when said first channel-cut crystal diffracts the X-ray in the arrangement of (+, −).

7. The X-ray wavelength measurement apparatus according to claim 4 wherein:
the rotation center of said first channel-cut crystal is set in a position that allows X-ray to enter an identical plane of the opposing cut planes when said first channel-cut crystal diffracts X-ray in each of arrangements of (−, +) and (+, −).

8. The X-ray wavelength measurement apparatus according to claim 7, further comprising a rotation control mechanism for controlling the rotation of said first channel-cut crystal, wherein
said rotation control mechanism includes an angle detector having self-calibration function for detecting displacement of a scale position of a rotation angle.

9. The X-ray wavelength measurement apparatus according to claim 4 inclusive, further comprising a rotation control mechanism for controlling the rotation of said first channel-cut crystal, wherein
said rotation control mechanism includes an angle detector having self-calibration function for detecting displacement of a scale position of a rotation angle.

10. An X-ray wavelength measurement apparatus, comprising:
a first channel-cut crystal for wavelength measurement in which two opposing cut planes are so formed that at least a part of mutual projections thereof overlap with the cut planes;
a second channel-cut crystal for collimator which is arranged on the incident side of said first channel-cut crystal and in which two opposing cut planes are formed;
a detector for detecting the intensity of X-ray spectrally reflected by said first channel-cut crystal; and
a turntable for rotating said first channel-cut crystal with respect to said second channel-cut crystal such that a rotation center of said first channel-cut crystal is set to be capable of diffracting X-ray in respective arrangements of (−, +) and (+, −), wherein (+) or (−) is defined as a crystal arrangement which causes a same or opposite X-ray bending direction to a first X-ray bending direction of diffraction; and
said second channel-cut crystal diffracts X-ray at a crystal plane having the same index as that of a crystal plane at which said first channel-cut crystal diffracts X-ray, to guide the diffracted X-ray into said first channel-cut crystal.

11. The X-ray wavelength measurement apparatus according to claim 10, wherein said second channel-cut crystal is placed for fixing the rotation for incident X-ray upon carrying out wavelength measurement.

12. The X-ray wavelength measurement apparatus according to claim 11 wherein:
the rotation center of said first channel-cut crystal is set between said two opposing cut planes of said first channel-cut crystal or between extended planes of said two opposing cut planes of said first channel-cut crystal; and
a cut plane on which X-ray is incident when said first channel-cut crystal diffracts the X-ray in the arrangement of (−, +) differs from that on which X-ray is incident when said first channel-cut crystal diffracts the X-ray in the arrangement of (+, −).

13. The X-ray wavelength measurement apparatus according to claim 11 wherein:
the rotation center of said first channel-cut crystal is set in a position that allows X-ray to enter an identical plane of the opposing cut planes of said first channel-cut crystal when said first channel-cut crystal diffracts X-ray in each of arrangements of (−,+) and (+,−).

14. The X-ray wavelength measurement apparatus according to claim 10 wherein:
the rotation center of said first channel-cut crystal is set between said two opposing cut planes of said first channel-cut crystal or between extended planes of said two opposing cut planes of said first channel-cut crystal; and
a cut plane on which X-ray is incident when said first channel-cut crystal diffracts the X-ray in the arrangement of (−, +) differs from that on which X-ray is incident when said first channel-cut crystal diffracts the X-ray in the arrangement of (+, −).

15. The X-ray wavelength measurement apparatus according to claim 10 wherein:
the rotation center of said first channel-cut crystal is set in a position that allows X-ray to enter an identical plane of the opposing cut planes when said first channel-cut crystal diffracts X-ray in each of arrangements of (−,+) and (+,−).

16. The X-ray wavelength measurement apparatus according to claim 10, further comprising a rotation control mechanism for controlling the rotation of said first channel-cut crystal, wherein said rotation control mechanism includes an angle detector having self-calibration function for detecting displacement of a scale position of a rotation angle.

* * * * *